United States Patent [19]

Inagaki

[11] Patent Number: 4,940,157
[45] Date of Patent: Jul. 10, 1990

[54] METHOD OF TREATING MEDICAL WASTES AND CONTAINERS TO BE USED FOR THE TREATMENT METHOD

[76] Inventor: Jitsuo Inagaki, 71, Aza Kamiyashiki, Oaza Itsusiki, Itsusikicho Hazugun Aichi, Japan

[21] Appl. No.: 337,078

[22] Filed: Apr. 12, 1989

[30] Foreign Application Priority Data

Feb. 27, 1989 [JP] Japan .................... 1-43120

[51] Int. Cl.⁵ ............................................. B65D 51/18
[52] U.S. Cl. .................... 220/254; 220/256; 220/259; 220/335; 220/336; 220/344; 220/1 T; 206/366
[58] Field of Search .............. 220/215, 253, 254, 256, 220/259, 336, 344, 378, 465, 466, 1 T; 206/336, 365, 366, 370

[56] References Cited

U.S. PATENT DOCUMENTS

| | | | |
|---|---|---|---|
| 1,152,286 | 8/1915 | Brownson | 220/336 |
| 3,164,286 | 1/1965 | Kole | 220/336 |
| 3,860,111 | 1/1975 | Thompson | 220/253 X |
| 4,141,461 | 2/1979 | La Chance | 220/253 |
| 4,466,538 | 8/1984 | Gianni | 206/366 |
| 4,657,139 | 4/1987 | Hanifl | 220/336 |
| 4,667,821 | 5/1987 | Shillington | 206/366 |
| 4,802,579 | 2/1988 | Hall et al. | 206/366 |
| 4,807,344 | 2/1989 | Kelson et al. | 206/366 X |

Primary Examiner—Stephen Marcus
Assistant Examiner—Nova Stucker
Attorney, Agent, or Firm—Donald W. Hanson

[57] ABSTRACT

A method of safely treating medical wastes such as syringe needles, absorbent tissue and bandages, wherein all the steps of treatment from throwing medical wastes into the container to the final disposal are identified by the appearance of the container. There is also provided a disposable container that can be safely used with the method. A container according to the invention comprises a lid section provided with a certain amount of elastic filler material between an inner lid and a top lid, a pair of input ports provided on the lid section for throwing medical wastes therethrough and a pair of semi-circular rotary lids for opening and closing the input ports, wherein the input ports are provided with a larger opening and a smaller opening which is in communication with the larger opening and so dimensioned to come into engagement with the tip of a syringe so that the needle is removed from the syringe by pulling up the latter from the opening.

18 Claims, 7 Drawing Sheets

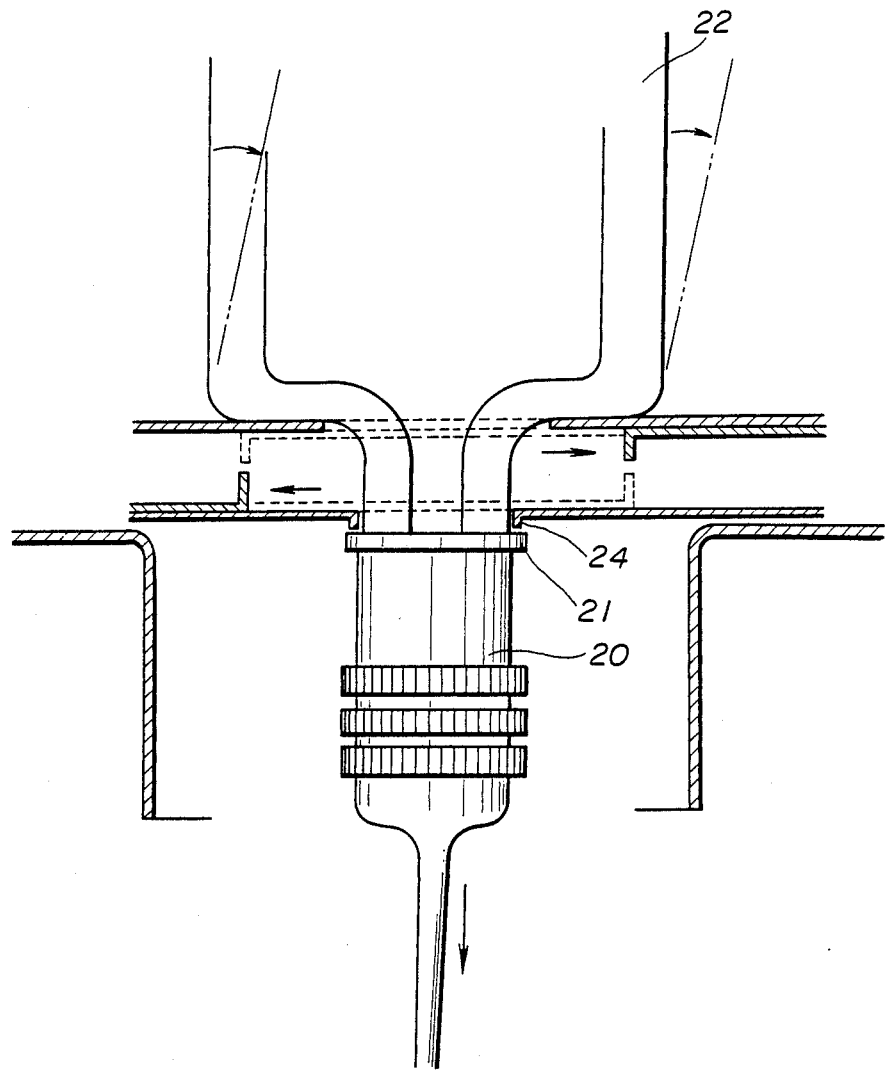

METHOD OF TREATING MEDICAL WASTES AND CONTAINERS TO BE USED FOR THE TREATMENT METHOD

BACKGROUND OF THE INVENTION

This invention relates to a method of treating medical wastes with which medical wastes such as waste syringes, absorbent tissues and bandages are safety treated and all steps of the treatment process from reception of wastes to completion of treatment are identified by the appearance of the containers involved and it also relates to a safe container to be used for the treatment method.

Currently, medical wastes such as syringes, absorbent tissues and bandages are thrown into containers such as boxes with an open upper end and then dumped into large containers by garbage collectors, who carry them to incineration and/or reclamation sites for disposal. With such a disposal system, however, medical wastes can be exposed to atmosphere and become contacted with garbage persons and/or other persons during transportation and/or disposal processes. Since medical wastes can be contaminated by highly toxic substances and/or infectious germs, garbage persons and other persons who deal with wastes are liable to be infected by such substances and germs through sores and wounds on the body. Thus, disposal of medical wastes has been attracting attention of the modern society at large and establishment of a safe disposal method has become a matter of high priority.

On the other hand, syringes that have been used for blood drawing and other purposes are normally thrown away with capped needles or after removing needles from the syringes. Again, such a practice of waste disposal is accompanied by a high risk of infecting medical personnel with B-type hepatitis virus and AIDS as needles can erroneous puncture the body of the personnel while they are capping the needles or the content of syringes can contaminate fingers and hands of the personnel when the needles are removed from the syringes. With a view to getting rid of these problems, various containers which are provided with a particular means for safely removing needles from used syringes have been proposed, although such a container entails a risk of shedding the blood contained therein once it is toppled down by mistake so that the blood can eventually come to contact with and contaminate human bodies and such a container is so designed that it is used only for syringe needles and can not be used for containing syringe bodies and other medical wastes.

BRIEF SUMMARY OF THE INVENTION

It is therefore an object of the present invention to provide a method of treating medical wastes which is free from all the above mentioned problems concerning medical wastes disposal and at the same time significantly enhances the safety level of medical waste disposal and to provide a container to be used for the method.

It is another object of the present invention to provide a method of treating medical wastes with which medical wastes are treated without requiring operators to touch them and hence without any risk of contaminating waste operators with infectious germs and to provide a container to be used with the method.

It is still another object of the present invention to provide a container for treating medical wastes that can safely treat medical wastes without any risk of the blood and toxic fluid materials in the containers flowing away therefrom.

It is still a further object of the present invention to provide a container for treating medical wastes with which used syringes can be thrown into it without any risk of operators touching the blood contained in the syringes.

It is still a further object of the present invention to provide a method of treating medical wastes with which containers for treating medical wastes can be identified by appearance concerning at what stage of treatment each of the containers is used such as transportation, heat sterilization and post-treatment and to provide containers to be used for the method.

Other objects as well as advantages of the present invention will be become apparent in the following description which is made by referring to the accompanying drawings.

BRIEF DESCRIPTION OF THE DRAWINGS

FIG. 9 is a sectional view of the embodiment of FIG. 1 illustrating how the needle is removed from the syringe.

DETAILED DESCRIPTION OF THE INVENTION

The above objects of the present invention are achieved by providing a method of treating medical wastes comprising a step of throwing medical wastes into a metal container provided with a pair of input ports that can be hermetically closed and a certain of elastic filler material that can be burnt or melted between a top lid and an inner lid, a step of fitting a plastic cap on the top lid after the container is filled with medical wastes, a step of transporting and throwing the container into an incinerator to burn or melt said filler material to release the air-tight condition of the lid section of the container so that the wastes are heated and sterilized and a step of pressing the wastes for land reclamation or sorting the wastes for recycling of resources.

According to the present invention, there is provided a container comprising a lid section provided with a certain amount of elastic filler material between an inner lid and a top lid rigidly fitted to an opening of the container, a pair of input ports provided on said lid section for throwing medical wastes therethrough and a pair of semi-circular rotary lids for opening and closing said input ports, wherein said input ports are provided with a larger opening and a smaller opening which is in communication with the larger opening and so dimensioned to come into engagement with the tip of a syringe so that the needle is removed from the syringe by pulling up the latter from the opening.

Now the invention will be described by referring to preferable embodiments of the invention illustrated in the accompanying drawings.

Figure 1:
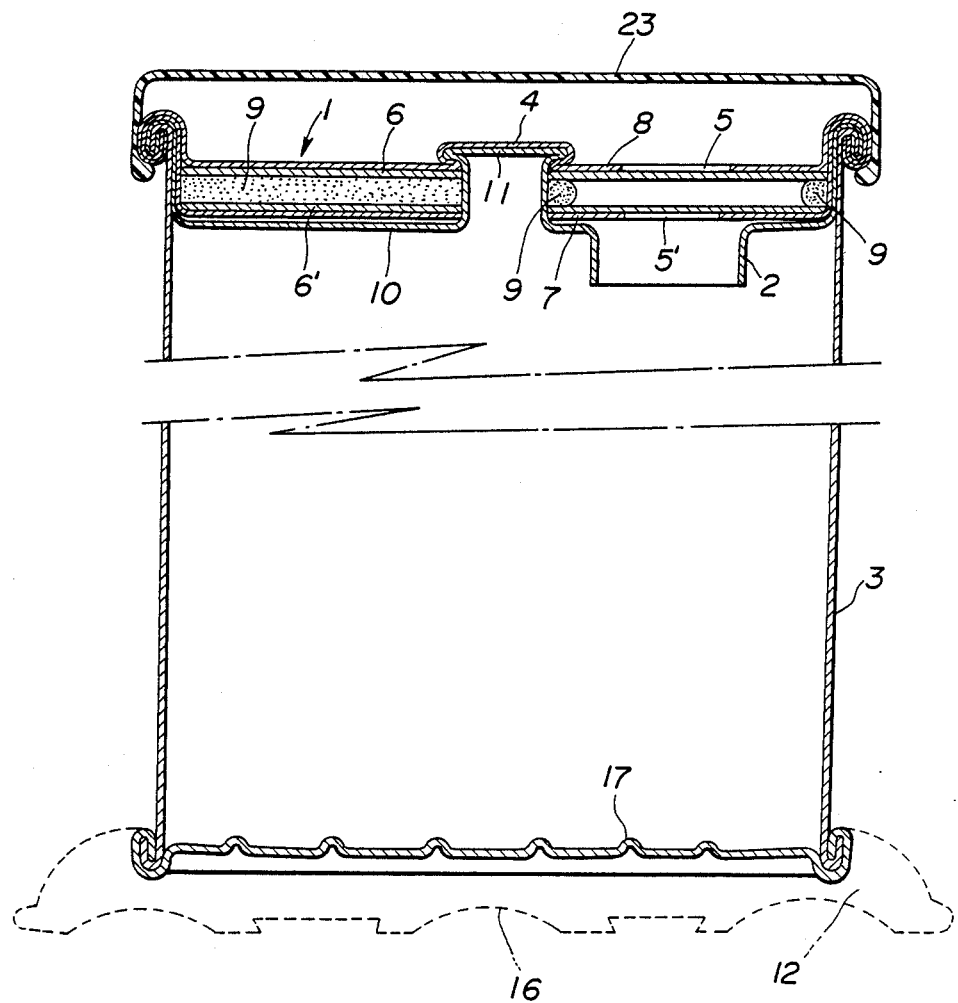
FIG. 1 is a sectional view of an embodiment of the present invention cut along V—V line of FIG. 5.

FIG. 1 of the accompanying drawings shows a sectional view of the embodiment which comprises a cylindrical metal container 3 (which can be securely fitted on a rubber-made stand 12 having suction disks 16 at the bottom as illustrated by dashed lines in the drawing), a circular lid section 1 fitted on the top of the container, a pair of input ports 5, 5' formed on the lid section 1 and a pair of semi-circular rotary lids 6, 6' for opening and closing said input ports 5, 5'.

Said circular lid section 1 is provided with a certain amount of filler material 9 and a pair of rotary lids 6, 6' located between a circular middle lid 7 and a circular top lid 8 as well as a circular inner lid 10 rigidly fitted under said middle lid 7. A projection 11 standing upward at the center of said inner lid 10 is formed and comes into engagement with a bore formed around said semi-circular rotary lids 6, 6'. A similar projection 4 standing upward on the circular top lid 8 is also formed and the two projections are securely connected together by means of a caulking technique by which the two projections are brought to contact with each other and then crushed in order to realize an airtight condition of the container. The peripheries of the inner lid 10, the middle lid 7 and the top lid 8 are held standing upward and then rolled in together with the upper edge of the container in order to hermetically seal the container as in the case of sealing a can.

Figure 4:
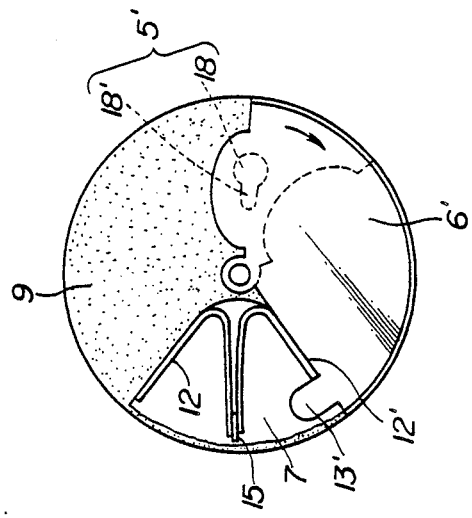
FIG. 4 is a plan view of the embodiment of FIG. 1 with the top lid, the filler material for securely holding the top lid and the rotary lid for opening and closing the input port provided on the top lid taken away from the container.
Figure 2:
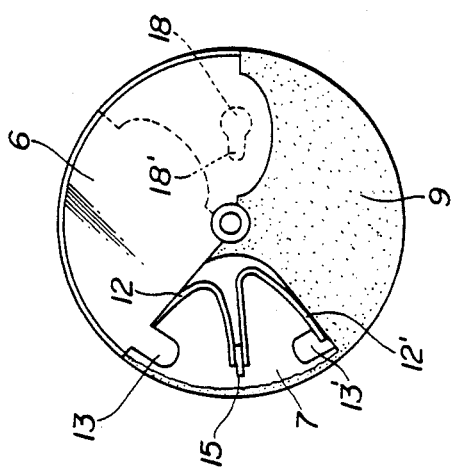
FIG. 2 is a plan view of the embodiment of FIG. 1 with the top lid taken away from the container.

As illustrated in FIG. 4, a certain amount of filler material 9 is securely fitted to the upper side of the circular middle lid 7 in the form of a sector and, as illustrated in FIG. 2 a corresponding amount of filler material 9 is also securely fitted to the lower side of the circular top lid 8 in the form of a sector. Then, as illustrated in FIGS. 2 and 4, a pair of semi-circular rotary lids 6, 6' are provided between the circular middle lid 7 and the circular top lid 8. As filler material, a sealing material, rubber, synthetic resin or other elastic materials that can be burnt or melted by heat may be used. The filler material has the role of keeping the semi-circular rotary lids 6, 6' in close contact with the opening so that the liquid content of the container is prevented from flowing out even when the container is toppled and of allowing ejection of the vapor generated in the container through the input ports 5, 5' as it is burnt or melted.

Figure 3:
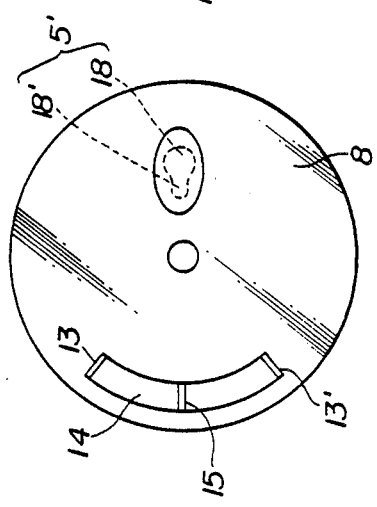
FIG. 3 is a plan view of the embodiment of FIG. 1.

The semi-circular rotary lids 6, 6' block their respective input ports and one of the edges of each lid is closely and elastically in contact with the elastic filler material while the other edges respectively abut a pair of angle springs 12, 12' by way of a stopper 15 rigidly fitted to the middle lid 7 and the other edges of the angle springs respectively abut the corresponding stepped portions of the filler material. The edges of the semi-circular rotary lids 6, 6' that abut the angle springs are respectively connected with strips 13, 13' which are standing up and, as shown in FIG. 3, projecting from an curved slit 14 formed on the top lid. The stopper 15 is rigidly fitted to the middle lid 7 and located at the middle of the curved slit 14. The input port 5' is so shaped that a large opening 18 and a small opening 18' are connected together and the small opening 18' comes into tight engagement with the tip of a syringe. The large opening 18 has the role of guiding a syringe needle to the small slit 18' and providing an input port 5 for medical wastes such as used syringes and absorbent tissue. The size of the large opening 18 may be modified depending on the size of medical wastes the container is expected to accept.

As shown in FIG. 1, a short cylindrical downward projection 2 is integrally formed with lid section around the opening which is in communication with said input ports 5, 5' of the inner lid 10. With such an arrangement, the container can safely prevent the liquid content such as blood from flowing out through the input ports even when the container is toppled.

As shown in FIG. 1, a circular ridge 17 is formed at the bottom of the cylindrical iron container 3 in the above described embodiment. This ridge is intended to prevent the syringe needles thrown into the container from scattering and accumulate them within a limited area in the container.

Figure 6:
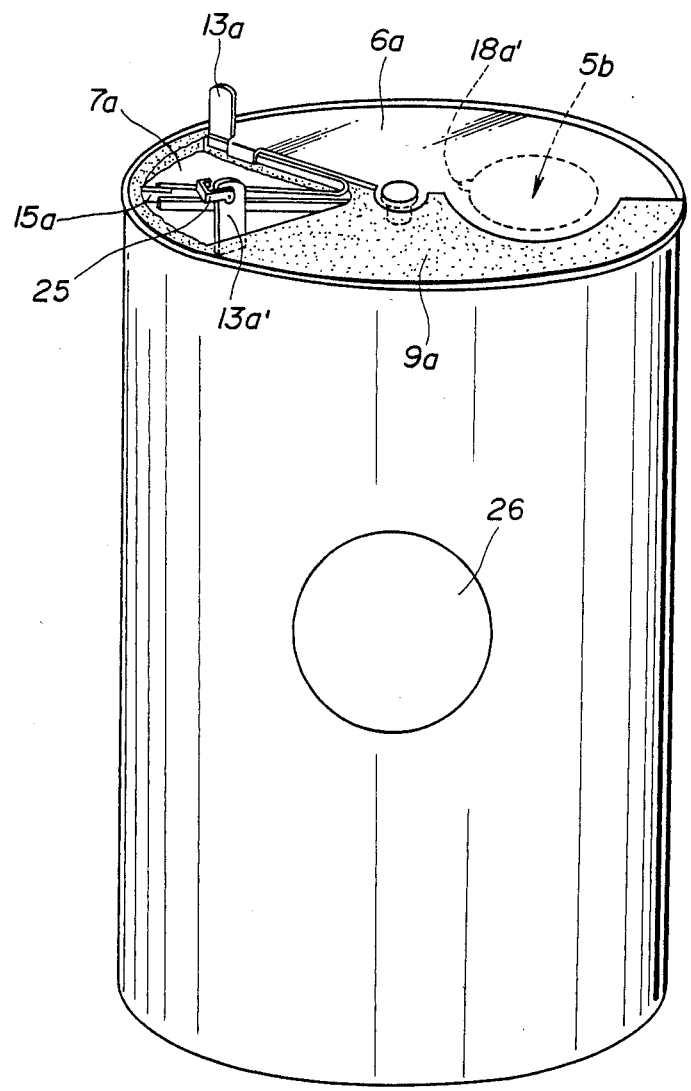
FIG. 6 is a perspective view of an another embodiment of the present invention with the top lid taken away from the container.
Figure 10:
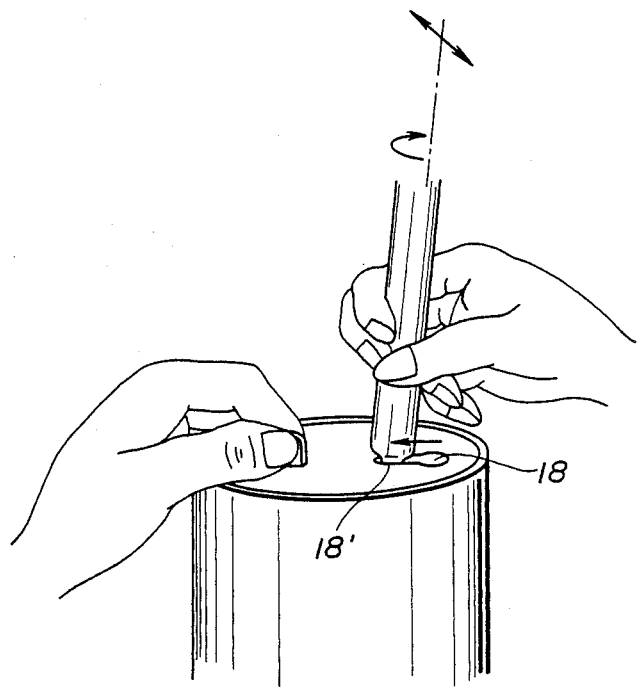
FIG. 10 is a perspective view of the embodiment of FIG. 1 illustrating how the needle is removed from the syringe.

In FIG. 6 which shows another embodiment of the invention, opening 5b is so formed that it is large enough to accept any medical wastes, while narrow slit 18a' has a size appropriate for removing needles from syringes.

In the above embodiment, a pair of semi-circular rotary lids 6a, 6a' are provided between a middle lid 7a and a top lid as in the case of the first embodiment.

Figure 7:
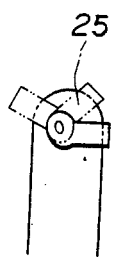
FIG. 7 is a side view of the cap of the container of the present invention designed to securely hold the strip.
Figure 8:
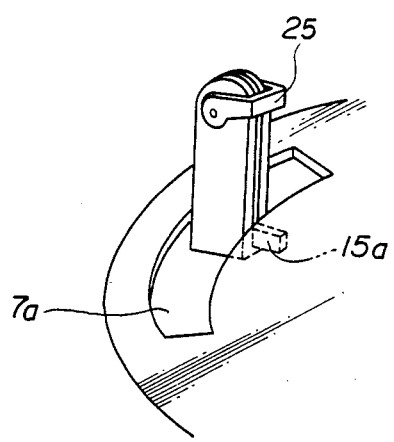
FIG. 8 is a perspective view of the strip of FIG. 7 securely fitted to the cap.

As shown in FIGS. 7 and 8, a U-shaped connector 25 is rigidly fitted to one of a pair of strips 13a, 13a' for opening and closing the large opening so that, when the strips are held together by way of a stopper 15a standing on the middle lid 7a by moving the connector 25 from the position as shown by the dotted line to the position shown by the solid line, the large opening 5b is kept wide open to accept medical wastes. Since a narrow slit 18'a is so formed that it is in communication with the large opening 5b, needles can be removed from syringes by utilizing this slit 18'a.

When a container according to the invention is marked by a specific symbol such, as a symbol for clinics or by a specific color at spot 26 on the exterior periphery of the container as shown in FIG. 6, it will be easily identified as a container for medical wastes. It may be convenient that the container is also marked by a heat-resistive paint such as a silicone paint that is not inflammable below a certain temperature so that if the container has been treated by heat at a temperature at which the content is completely sterilized can be visually determined.

Now the method of treating medical wastes using a container according to the invention will be described.

Figure 5:
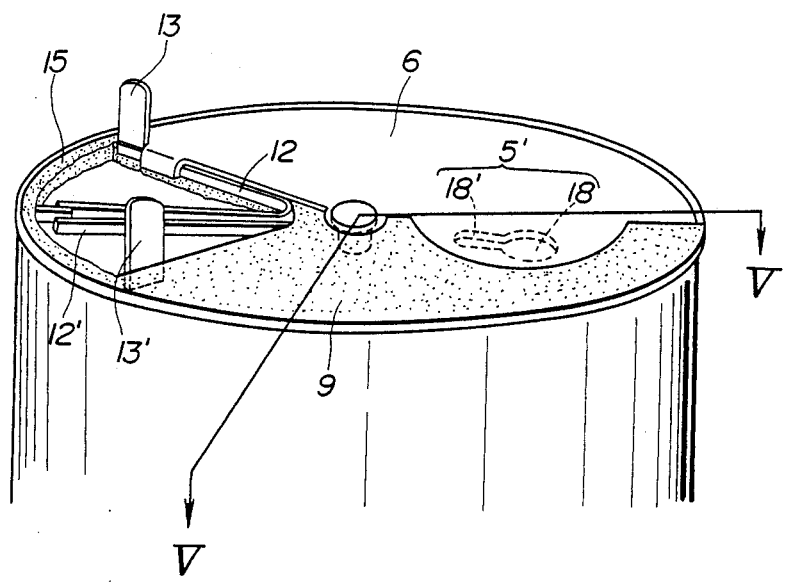
FIG. 5 is a partial perspective view of the embodiment of FIG. 1 with the top lid taken away from the container.

As shown in FIG. 5, the two strips 13, 13' are held together and the semi-circular rotary lids 6, 6' are rotated to open the input ports 5, 5' to accept medical wastes.

Figure 11:
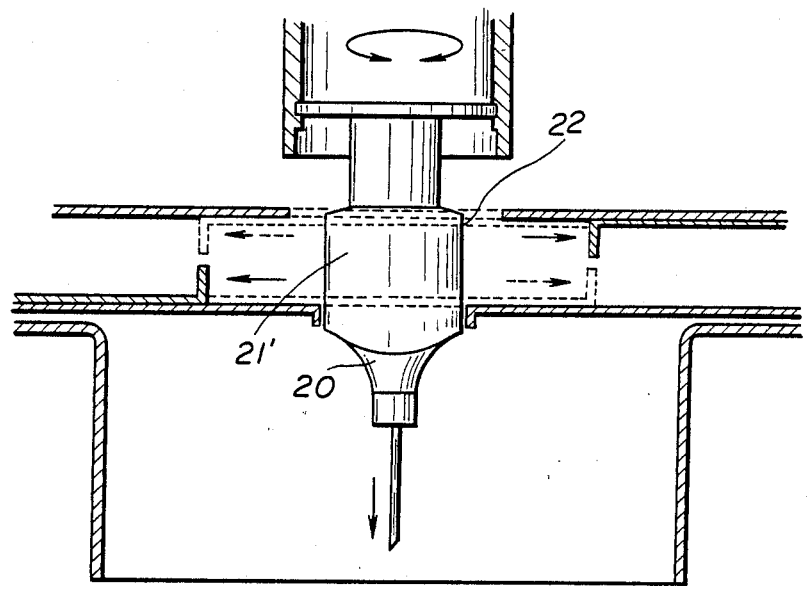
FIG. 11 is a sectional view of the embodiment of FIG. 1 illustrating a condition where the needle is removed from the syringe and the rotary lid is moved.
Figure 12:
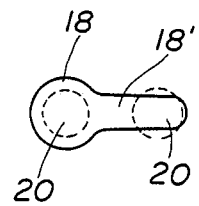
FIGS. 12 and 13 are plan views of the embodiment of FIG. 1 illustrating how the needle is removed from the syringe by way of the input ports.
Figure 13:
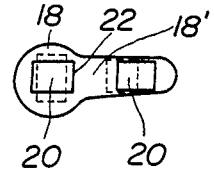

Medical wastes other than syringe needles such as used gauze, absorbent tissue and syringe bodies are thrown into the container by way of large opening 18, while needles are removed from syringes by utilizing the narrow slit 18' and dropped into the container. To remove a needle of the regular type as shown in FIGS. 9 and 12, the needle 20 is brought to the large opening 18 and then moved to the narrow slit 18' so that the root 21 of the needle 20 comes in contact with the peripheral projection 24. When portion 22 of the syringe is tapped and inclined in the direction as shown by the arrow, the needle 20 is taken away from the syringe as it acts as a lever and the needle falls into the container. On the other hand, to remove a needle of a lock-type syringe as shown in FIGS. 11 and 13, the needle 20 is brought to the large opening 18 and then moved to the narrow slit 18'. When the syringe 22 is rotated, the square root section 21' on the needle comes to be held by the side wall of the slit and the needle eventually falls down into the container as it is unscrewed from the syringe. When the container becomes full of medical wastes, the plastic lid body 23 is put on the top of the container to seal it and the container is transported to the incinerator. When the container is thrown into the incinerator of two stage burning and completely odorless fume type, the plastic lid body 23 is burnt and the filler material is either burnt or melted to release the airtightness of the opening and allow evaporation of the liquid within the container so that inflammable vapor in the container may also burn. While the vapor is burning, the silicone paint is checked to see if it has been burnt off from the container, an indication that the contents have been completely sterilized. Then, the container is pressed for land reclamation or treated for recycle of useful resources.

As described above, by using the method according to the present invention, medical personnel and garbage collectors are free from any risk of being contaminated by germs and toxic substances as they are kept away from touching medical wastes during treatment and disposal stages of the wastes. Moreover, the container according to the present invention is provided with safety measures to prevent any toxic substances such as infected blood in the container from flowing out even when the container is toppled and to ensure safe disposal of syringe needles by medical personnel without requiring them to touch the needles, an additional safety scheme to prevent the personnel from touching infected blood. Furthermore, a container according to the invention is designed to be identified by its appearance in terms of the stages of treatment including service, transportation, heat sterilization and final disposal.

What is claimed is:

1. An article for treatment of medical wastes comprising a container having an opening, a lid section including a certain amount of elastic filler material between an inner lid and a top lid and rigidly fitted into the opening of the container, a pair of input ports provided on said lid section for disposing medical wastes therethrough and a pair of rotary lids for opening and closing said input ports, wherein said input ports are provided with a larger opening and a smaller opening which is in communication with the larger opening and so dimensioned to come into engagement with a needle of a syringe so that the needle can be removed from the syringe by pulling up the syringe from the opening.

2. An article for treating medical wastes according to claim 1, wherein the inner lid includes a port and a downward cylindrical projection is formed about the port on said inner lid to prevent liquid content in said container from flowing out even when the container is toppled.

3. An article for treating medical wastes according to claim 1, further including a middle lid adjacent to the inner lid.

4. An article for treating medical wastes according to claim 3, wherein one port is formed in a middle lid and one port is formed in the top lid.

5. An article for treating medical wastes according to claim 3 wherein said rotary lids are between said middle lid and said top lid.

6. An article for treating medical wastes according to claim 3, wherein the peripheries of the inner lid, the middle lid and the top lid are secured to the opening of the container.

7. An article for treating medical wastes according to claim 6, wherein the peripheries of the inner lid, the middle lid and the top lid are rolled about the opening of the container.

8. An article for treating medical wastes according to claim 3, wherein the inner lid has a central projection which projects through a bore in said rotary lids.

9. An article for treating medical wastes according to claim 8, wherein said top lid has a central projection over and secured to the projection of the inner lid.

10. An article for treating medical wastes according to claim 9, wherein said top lid has a curved slit and each rotary lid has a strip projecting through the slit in the top lid.

11. An article for treating medical wastes according to claim 10, wherein the middle lid includes a stopper and each rotary lid abuts spring means in contact with the stopper.

12. An article for treating medical wastes according to claim 11, wherein one strip includes a connector for releasably securing the two strips together.

13. An article for treating medical wastes according to claim 14, wherein the middle lid includes a stopper and each rotary lid abuts spring means in contact with the stopper.

14. An article for treating medical wastes according to claim 14, wherein said top lid has a curved slit and each rotary lid has a strip projecting through the slit in the top lid.

15. An article for treating medical wastes according to claim 14, wherein the middle lid includes a stopper and each rotary lid abuts spring means in contact with the stopper.

16. An article for treating medical wastes according to claim 14, wherein one strip includes a connector for releasably securing the two strips together.

17. An article for treating medical wastes according to claim 16, wherein the connector is U-shaped.

18. An article for treating medical wastes according to claim 1, wherein the container has a circular ridge on an interior surface opposed to the opening.

* * * * *